(12) United States Patent
Wang et al.

(10) Patent No.: US 6,940,286 B2
(45) Date of Patent: Sep. 6, 2005

(54) ELECTRICAL IMPEDANCE TOMOGRAPHY

(75) Inventors: Mi Wang, Cheshire (GB); Wuliang Yin, Manchester (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 10/250,327

(22) PCT Filed: Dec. 28, 2001

(86) PCT No.: PCT/GB01/05636

§ 371 (c)(1),
(2), (4) Date: Feb. 4, 2004

(87) PCT Pub. No.: WO02/053029

PCT Pub. Date: Jul. 11, 2002

(65) Prior Publication Data

US 2004/0130338 A1 Jul. 8, 2004

(30) Foreign Application Priority Data

Dec. 30, 2000 (GB) ............................................. 0031854
Aug. 25, 2001 (GB) ............................................. 0120772

(51) Int. Cl.⁷ ........................ G01N 27/28; G01R 27/02
(52) U.S. Cl. ...................... 324/450; 324/603; 324/605; 600/547; 600/393; 378/21
(58) Field of Search .............................. 324/439–450, 324/600, 605, 609, 629; 600/393, 547; 378/21

(56) References Cited

U.S. PATENT DOCUMENTS

| | | | |
|---|---|---|---|
| 4,486,835 A | 12/1984 | Bai et al. ....................... | 378/21 |
| 4,617,939 A | 10/1986 | Brown et al. ................ | 600/547 |
| 4,920,490 A | 4/1990 | Isaacson ...................... | 600/547 |
| 5,272,624 A | 12/1993 | Gisser et al. ................ | 600/547 |
| 6,501,984 B1 * | 12/2002 | Church et al. ............... | 600/547 |

FOREIGN PATENT DOCUMENTS

| | | |
|---|---|---|
| EP | 2019579 A | 10/1979 |
| EP | 2119520 A | 11/1983 |
| EP | 2160323 A | 12/1985 |
| WO | WO 95/24155 | 9/1995 |
| WO | WO 98/23204 | 6/1998 |

OTHER PUBLICATIONS

International Search Report dated Mar. 25, 2002 for PCT/GB01/05636.

Wang et al. "Modelling and analysis of electrically conducting vessels and pipelines in electrical resistance process tomography," *IEE Proc.–Sci. Meas. Technol.*, vol. 412, No. 4, Jul. 1995.

Dickin et al. "Electrical resistance tomography for process applications," *Measurement Science and Technology*, vol. 7, No. 3, Mar. 1, 1996, pp. 247–260.

(Continued)

Primary Examiner—Vincent Q. Nguyen
(74) Attorney, Agent, or Firm—Myers Bigel Sibley & Sajovec

(57) ABSTRACT

Methods and apparatus are provided for obtaining a representation of the distribution of electrical impedance within a multiphase flow with an electrically continuous or discontinuous principle flow contained within an electrically conductive solid ring electrode, including providing a plurality of mutually spaced electrical contacts mounted at the outside wall of the ring and electrically contacting with the ring, applying currents or voltages to the ring from the electrical contacts, generating a more homogeneous electric field distribution within the material, measuring voltage or current distribution alone the ring from other electrical contacts, relatively intensifying the imaging sensitivity at the central area of the sensing domain using a π/2 angle sensing strategy and reconstructing the representation of the impedance distribution using CG method with an error processing strategy.

25 Claims, 9 Drawing Sheets

OTHER PUBLICATIONS

Tai et al. "An experimental electrical impedance tomography system," *Proceedings of the Region Ten Conference*, Beijing, Oct. 19–21, 1993, vol. 3.

Seleghim et al. "Direct imaging of two-phase flows by electrical impedance measurements," *Measurement Science and Technology*, vol. 9, No. 9, Sep. 1998, pp. 1492–1500.

Wang et al. "Detecting non-uniform foam density using electrical resistance tomography," *Chemical Engineering Science*, vol. 54, 1999, pp. 707–12. No month available.

Geselowitz, David B. "An Application of Electrocardiographic Lead Theory to Impedance Plethysmography," *IEEE Transcations on Biomedical Engineering*, vol. BME–18, No. 1, Jan. 1971.

Yorkey et al. "Comparing Reconstruction Algorithms for Electrical Impedance Tomography," *IEEE Transactions on Biomedical Engineering*, vol. BME–34, No. 11, Nov. 1987.

Lehr, John, "Short Communications: A Vector Derivation Useful in Impedance Plethysmographic Field Calculations," *IEEE Transactions on Biomedical Engineering*, vol. BME–19, Mar. 1972.

Murai et al. "Electrical Impedance Computed Tomography Based on a Finite Element Model," *IEEE Transactions on Biomedical Engineering*, vol. BME–32, No. 3, Mar. 1985.

Wang et al. "Electrical Resistance Tomographic Sensing Systems for Industrial Applications," *Chem. Eng. Comm.*, 1999, vol. 175, pp. 49–70. No month available.

Barber et al. "Applied potential tomography," *J. Phys. E: Sci. Instrum.*, vol. 17, 1984, pp. 723–33. No month avail.

Lucas et al. "Measurement of the solids volume fraction and velocity distributions in solids–liquid flows using dual plane electrical resistance tomography," *Flow Measurement and Instrumentation*, vol. 10, 1999, pp. 249–58. No month.

Hoyle et al. "Multi–Sensor Process Tomography System Design: Part 1 –Systems and Hardware Engineering," $1^{st}$ *World Congress on Industrial Process Tomography*, Buxton, Greater Manchester, Apr. 14–17, 1999.

Brown et al. "Applied Potential Tomography –Data Collection Problems," *International Conference on Electric and Magnetic Fields in Medicine and Biology*, Dec. 4–5, 1985.

Dyakowski et al. "On–line monitoring of dense phase flow using real time dielectric imaging," *Powder Technology*, vol. 104, 1999, pp. 287–95. No month available.

Kotre, C.J. "EIT image reconstruction using sensitivity weighted filtered backprojection," *Phsiol. Meas.* vol. 15, 1994, pp. A125–A136. No month available.

Lucas et al. "Measurement of the solids volume fraction and velocity distributions in solids –liquid flows using dual–plane electrical resistance tomography," *Journal of Flow Measurement and Instrumentation*, Oct. 4, 1999. No month available.

* cited by examiner

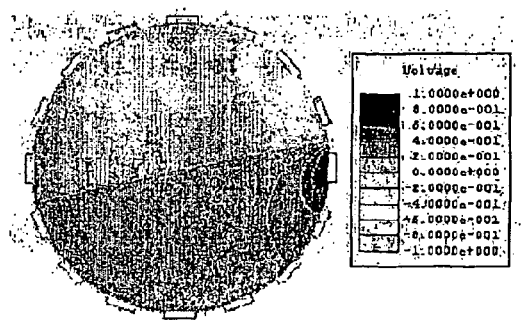
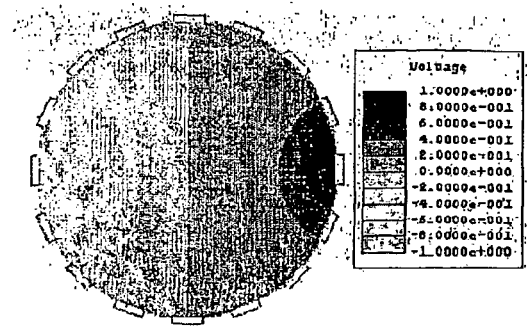
Fig. 4a Fig. 4b
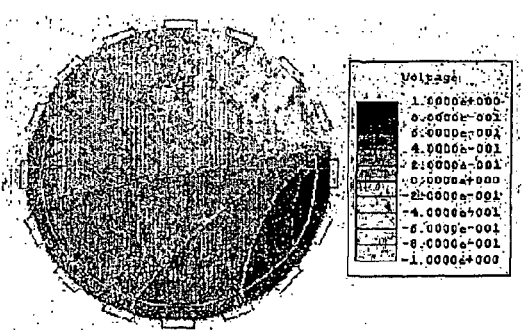
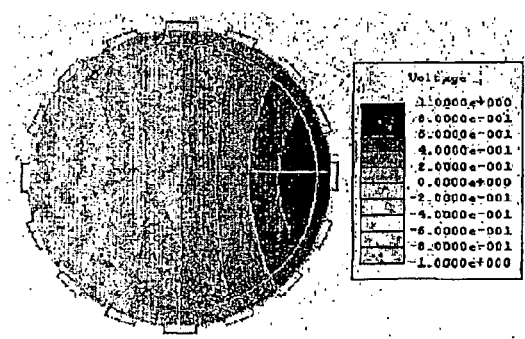
Fig. 5a Fig. 5b
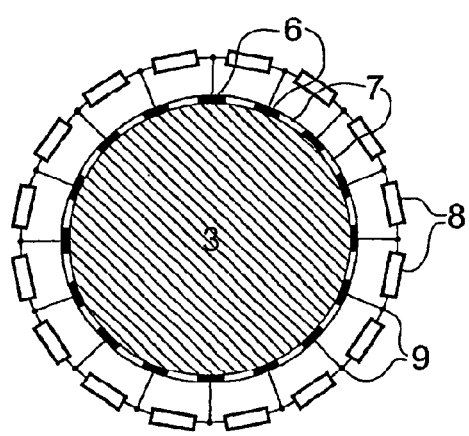
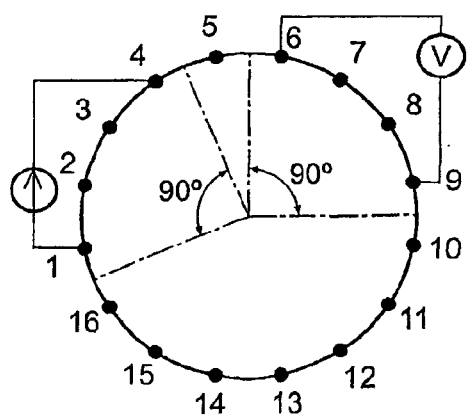
Fig. 6 Fig. 7

ELECTRICAL IMPEDANCE TOMOGRAPHY

RELATED APPLICATIONS

The present application is a 35 U.S.C. §371 national phase application of PCT International Application No. PCT/GB01/05636, having an international filing date of Dec. 28, 2001, and claiming priority to Great Britain Patent Application No. 0031854.3, filed Dec. 30, 2000 and Great Britain Application No. 0120772.9, filed Aug. 25, 2001, the disclosures of which are incorporated herein by reference in their entireties. The above PCT International Application was published in the English language and has International Publication No. WO 02/053029 A1.

BACKGROUND OF THE INVENTION

This invention relates to a method of measuring the distribution of electrical impedance of a multi-phase flow using an electrically conductive ring electrode, and to a method of determining the internal structure of a body which utilises such a method and a computer programme product adapted for determining the internal structure of a body.

The invention further relates to an apparatus adapted to measure the distribution of electrical impedance of a multi-phase flow using an electrically conductive ring electrode.

This invention relates in general to electrical impedance tomography (EIT), and in particular to a new sensor construction and apparatus, a sensing strategy and an algorithm for measuring flow with electrically continuous and discontinuous conductivity phase, such as the oil/gas/water multiphase flow and the bubbling formation or foam construction.

A number of sensor construction methods for EIT were proposed in previous patents, which were comprise of placing an array of spaced electrodes in direct contact with the human body or process fluid [GB2119520, GB2160323, U.S. Pat. No. 4,617,939], or in indirect contact with the human body coupled with electrolyte [GB2019579], a sponger [WO98/23204] or any other suitable liquid medium [U.S. Pat. No. 4,486,835] with conductivity matched to the typical expected conductivity of the object being measured. To obtain better distinction between a known conductivity and an unknown conductivity change in a body, a sensing method of the best pattern of currents was disclosed in U.S. Pat. Nos. 4,920,490 and 5,272,624, and a sensor arrangement using a number of electrically conductive compartment electrodes each separated from neighbouring compartments by an insulating partition was disclosed in WO98/23204. It has become known to apply EIT to vessels and pipelines made of electrically non-conductive material, such as acrylic or other plastic materials, or made of electrically conductive metallic materials (WO 95/24155). In the process applications of EIT, it was also known that the electrodes were mounted inside the vessels or pipelines, and electrically insulated from one another, so as to be directly in electrical contact with the contents within.

It is clear that previous EIT methods were based on utilising a number of discrete electrodes mounted at spaced locations of the wall, which had to be electrically insulated from one another and in electrical contact with body or material contained within the wall whether the wall is electrically non-conductive or conductive. The coupling materials used between the electrodes and the human body in the indirect contact method from previous knowledge, such as the. electrolyte and sponger, were purely purposed as an electrical coupling medium with a conductivity value comparable to that of the volume to be measured, which were neither suitable for flow measurement nor functioned as a part of sensing strategy for improving the measurement capability. The limitations from the discrete electrode structure have been observed in following aspects. Firstly, it can not provide a correct measurement from a fluid with a discontinuous phase of electrical conductivity since some of these electrodes have lost their electrical contact with the conductive phase of the fluid, e.g. a half filled horizontal stratified flow or a foam construction with a large bubbling formation [M. Wang and C. J. Young, Chem. Eng. Science, 54(5), 1999]. Secondly, it generates a very non-uniform distribution of the imaging sensitivity because high dense currents are always present at the domains near to the current injecting and sinking electrodes. The limited contact area of the electrodes also produces a large common voltage, which highly reduces the signal-to-noise ratio for the differential measurement adopted in most cases. In addition, it is difficult to present data with high repeatability from a sensor with discrete electrodes since the unstable performance of the contact impedance or the electrode-electrolyte interfaces. Finally, the intrusive construction of the electrodes in these sensors has obvious difficulties from its installation for satisfying most industrial environments.

The major features of this invention are to employ an electrically conductive ring with a conductivity value higher than that of the principle flow [FIG. 1] as a tomographic sensor to supply a continuously electric current flow to the sensing domain, generate a more homogeneous imaging sensitivity distribution over the sensing domain and provide a smooth sensing surface without the obstruction effects to the flow. A PI/2 sensing strategy as an additional part of the invention further improves the imaging sensitivity distribution and an image reconstruction algorithm accompanied with the invention provides a practical solution for eliminating hardware noise in EIT applications.

SUMMARY OF THE INVENTION

The object of the invention is to provide a sensing method and apparatus with an improved imaging sensitivity distribution for measuring the electrical impedance distribution in a principle flow with an electrically continuous or discontinuous phase and a practically applicable accurate reconstruction algorithm for flow measurement.

Thus according to the invention we provide a method of measuring the distribution of electrical impedance of a multi-phase flow, of which the principal flow has an electrically continuous or discontinuous phase, using an electrically conductive ring electrode, characterised in that the ring electrode uses a PI/2 sensing strategy.

The ring electrode may have a much higher conductivity compared to-the-principle flow or materials to be measured and it is employed as said a ring electrode of a part of the sensor body. A more homogeneous electric field distribution can be produced if the conductivity of the electrical conductive ring is much higher than that of the target content. The electrically conductive ring may be made of solid substances such as a kind of metal, conductive rubber or ceramics.

A number of electrical contacts may be embedded into the conductive ring electrode in good electrical contact with the outside wall of the ring electrode or penetrated through the wall of the ring electrode in good electrical contact with the wall. The size of the contacts can be very small and the amount of the contacts can be installed to be much more than those in previous sensors. The sensitivity distribution is relatively intensified at a particulate interested area in the whole sensing domain, based on a specific sensing strategy or a combination of a basic set of independent measurements.

The sensor geometry and its conductivity can be optimized for the objective that the condition number of the sensitivity matrix becomes less and the sensitivity field becomes more homogenous.

The method of the invention may be especially useful in determining the structure of; for example, process materials, such as a process fluid or a part of a human body, with electrically continuous phase such as that in a miscible liquid or discontinuous phase such as that in a foam formation or a half filled horizontal oil/water/gas stratified flow.

The method may be extended to a sensor with discrete electrode structure using an external resistor network connecting all electrodes. Furthermore a multi-step image reconstruction algorithm using an error processing method is employed to reconstruct the conductivity distribution.

According to a yet further feature of the invention we provide a computer programme product adapted for determining the internal structure of a body with electrical impedance tomography characterised in that the programme includes the use of the algorithm $$\frac{\Delta V_j}{V_j} \approx -\frac{\sum_{k=1}^{w} \Delta\sigma_k s_{j,k}(\sigma_k)}{\sum_{k=1}^{w} \sigma_k s_{j,k}(\sigma_k)} \quad \text{(Equation 6)}$$

$(\Delta\sigma_k \ll \sigma_k, j = 1, 2, \ldots, P)$

Where j is the measurement-projection location and k is the pixel number, $s_{j,k}$ denotes the sensitivity coefficient at pixel k under the measurement-projection j, P denotes the maximum number of measurements, w denotes the maximum number of pixels, $\sigma_k$ and $\Delta\sigma_k$ are the conductivity and conductivity change at pixel k, respectively, and $V_j$ and $\Delta V_j$ are in respect to the reference voltage and the voltage change at measurement-projection j.

The solution of above equation can be implemented by assembling an inverse matrix using finite-step CG method so that the on-line image reconstruction only involves the multiplication of a matrix and a vector.

We also provide an apparatus adapted to measure the distribution of electrical impedance of a multi-phase flow of which the principal flow has an electrically continuous or discontinuous phase, using an electrically conductive ring electrode characterised in that the ring electrode is adapted to use a PI/2 sensing strategy.

BRIEF DESCRIPTION OF THE DRAWINGS

The invention will now be illustrated by way of example only and with reference to the accompanying drawings, in which

FIG. 4 shows two simulated electric field distributions with equi-potential lines from the sensor with discrete electrodes;

FIG. 5 shows two simulated electric field distributions with equi-potential lines from the sensor with an electrically conductive ring with conductivity ten times as that of the principle flow/material to be measured;

FIG. 6 shows an extension of the invention using a resistor network for a sensor with discrete electrode construction;

FIG. 7 shows a sensing strategy with a π/2 (90°) separation angle for measurement and excitation;

DETAILED DESCRIPTION OF EMBODIMENTS

Figure 1:
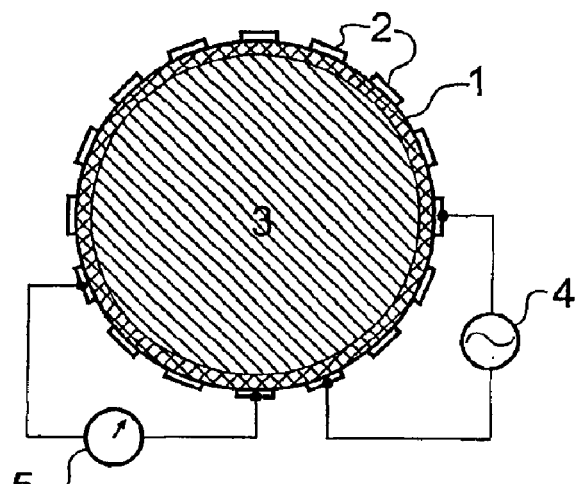
FIG. 1 illustrates the basic construction of the invention.

The electrically conductive ring sensor basically consists of an electrically conductive ring 1, a number of electrical contacts 2, a target content 3, a number of electrical excitation sources 4 and a number of voltage measurement devices 5 [FIG. 1].

Figure 2:
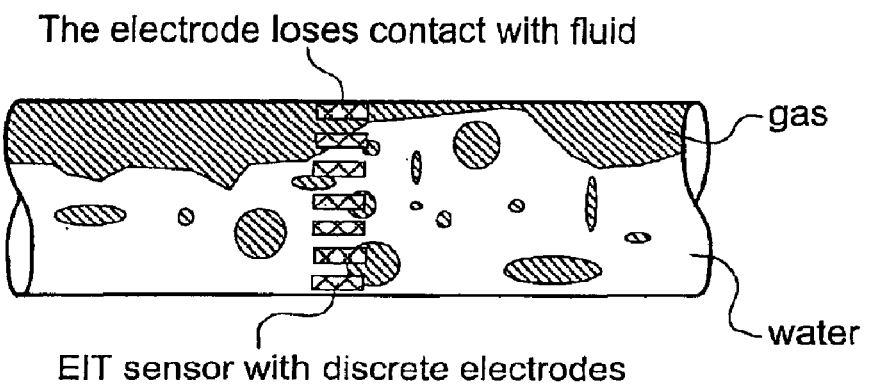
FIG. 2 illustrates a traditional EIT sensor under a stratified flow.
Figure 3:
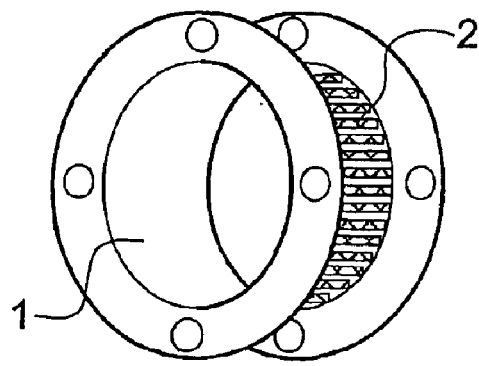
FIG. 3 illustrates a flange construction of the sensor.

The electrically conductive ring 1 is made of solid substances such as a kind of metals or alternatively, other electrically conductive materials such as conductive rubber or ceramic-metal with a conductivity value much higher than that of the content 3 to be measured. The electrically conductive ring acts as an 'continuous electrode' to distribute the electrical current flow and generate an electric field for mapping the impedance distribution of the content 3 due to applying currents from the metallic contacts 2. The metallic contacts 2 are embedded into the electrically conductive ring in good electrical contact with the outside wall of the electrically conductive ring. The size of these contacts 2 may be very small since a low common voltage on the contacts is produced from the high conductive ring 1 and there is no effects of electrode-electrolyte interface between these contacts 2 and the electrically conductive ring 1 if the ring is made of solid substance. Therefore, the amount of the contacts to be installed could be much more than the number of discrete electrodes in the conventional sensors. A number of electrical excitation sources, such as the currents or voltages 4, are applied to one or more electrical contacts 2. Boundary voltages or currents are also measured from the electrical contacts 2. A continuous electric field distribution presents along the inner surface of the electrically conductive ring that is in electrical contact with the target content 3. The target content 3 may be a process fluid with electrically continuous phase, such as that in a miscible liquid mixing, or with electrically discontinuous phases, such as those in oil-water-gas flow or froth formation [FIG. 2]. Since no discrete electrode directly contact to the target content 3, the excitation and measurement will not get into saturation under a certain current value when apart of the inner sensing surface loses an electrical contact to the principle flow. FIG. 3 illustrates its flange configuration.

A more homogeneous electric field distribution can be produced if the conductivity of the electrically conductive ring 1 is higher than that of the target content 3. Comparisons of the potential distributions generated from a sensor with discrete electrodes (FIGS. 4a and 4b) and the electrically conductive ring sensor (FIGS. 5a and 5b) are given, which were simulated using Ansoft Maxwell 2D simulator [Version 1-7-66, 1996, Ansoft Corporation]. In the simulation, the conductivity of the electrically conductive ring was ten times as that of the target content. The potential distributions in FIGS. 4a and 5a were generated from a current excitation between an adjacent electrode/contact pair. FIGS. 4b and 5b are potential distributions relating to an opposite electrode/contact pair excitation position. The potential distributions in FIGS. 5a and 5b are more equal-spaced than those given in FIGS. 4a and 4b. It is well known that the field-stream lines can be derived from the equal-potential lines based on the orthogonal method. Therefore, the simulation demonstrates that the electric field intensity distribution generated from the electrically conductive ring sensor are more uniform than that generated from a discrete electrode sensor if the conductivity of the ring 1 is high than the conductivity of the target content 3.

With the previous sensor construction [FIG. 6], a number of discrete electrodes 6 were intrusively embedded into a non-conductive vessel 7 with good electrical insulation between each other and electrically contact the target content 3. For a fluid with discontinuous phases of electrical conductivity, such as a half filled horizontal stratified flow or a foam construction with a large bubbling formation, it could not provide sufficient measurements since some of electrodes have lost their electrical contact with the conductive phase of the fluid [FIG. 2]. But for a conductive ring sensor, the current is always continuous even in situation like FIG. 2. As an extension of the invention, a resistor network 8 is proposed for such sensors with discrete electrode structure to perform a completed set of measurements. These electrodes are connected with the resistor network 8 using electrically conductive wires 9. The resistor network 9 plays a similar role as the electrically conductive ring 1, which bypasses and re-distributes currents in case of the current excitation electrodes blocked by a discontinuous fluid or bubbles, and produces a more homogeneous electric field than that produced from a conventional discrete electrode sensor. FIG. 6 shows the extension for the sensor with discrete electrodes.

The measurement relationship between one and other sensing strategies for a 4-electrode measurement protocol can be derived as Equation 1 & 2 based on the reciprocity theorem [Geselowitz, *IEEE Trans. Biomed Eng.* BME-18], which may be summarised as 'with a 4-electrode measurement protocol, the boundary measurements and the sensitivity matrix for an alternative sensing strategy can be derived from the complete set of independent measurements and the sensitivity matrix obtained from a known sensing strategy'. The measurements based on the alternative sensing strategy can not generate any more new information than that given from the complete set of independent measurements, but could produce a different signal-to-noise ratio and a different sensitivity distribution over the imaging domain. A general form of the boundary voltage relationship between an alternative 4-electrode sensing strategy and adjacent sensing strategy can be expressed as Equation 1, which derives mutual impedance or boundary voltages for an alternative 4-electrode sensing strategy from those for adjacent electrode pair strategy.

$$Z_{I,J}(I_{M,N}) = \sum_{m=M}^{N-1} \sum_{i=I}^{J-1} Z_{i,i+1}(I_{m,m+1}) \qquad \text{(Equation 1)}$$

$(1 \leq M < N < I < J \leq \text{number of electrode})$

Where $Z_{I,J}(I_{M,N})$ represents the mutual impedance obtained from voltage measured between electrode I and J when current presents between electrode M and N.

The sensitivity matrix of an alternative sensing strategy can also be derived from algebraic combination of the sensitivity matrix obtained from a complete set of independent measurements because a linear approximation is adopted in the calculation of the sensitivity matrix, and the linear relationship between the two sets of boundary voltages exist Equation 1). Derivation to a new sensitivity matrix for an alternative strategy from the sensitivity matrix of adjacent electrode pair strategy is given in Equation 2.

$$s_{I,J,k}(I_{M,N}) = \sum_{m=M}^{N-1} \sum_{i=I}^{J-1} s_{i,i+1,k}(I_{m,m+1}) \qquad \text{(Equation 2)}$$

$(1 \leq M < N < I < J \leq \text{number of electrodes})$

Where $S_{I,J}(I_{M,N})$ represents the sensitivity coefficient at pixel, k, obtained from the measurement and excitation position where the voltage is measured between Electrode I and J when current presents between electrode M and N.

Based on Equation 2, a sensitivity distribution with improved homogeneity, especially at the central area, has been found from a sensing strategy that the angle between two electrodes/contacts for measurement and excitation is $\pi/2$. This $\pi/2$ spaced sensing strategy is demonstrated in FIG. 7, which gives a total of 72 independent measurements.

Figure 8:
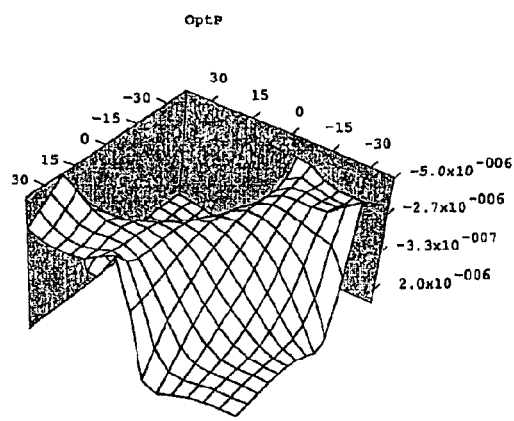
FIG. 8 is the sensitivity distribution from the voltage measurement opposite to the current excitation using the π/2 sensing strategy.
Figure 9:
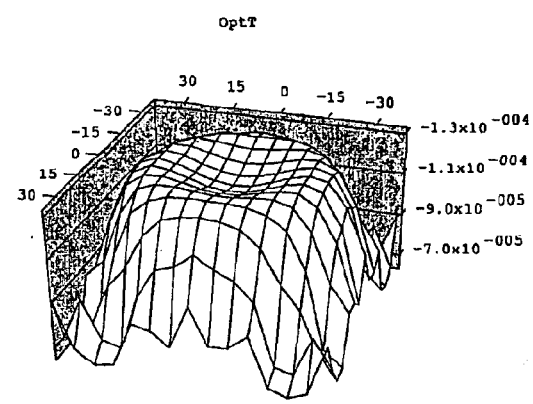
FIG. 9 is the overall sensitivity map using the π/2 sensing strategy.
Figure 10:
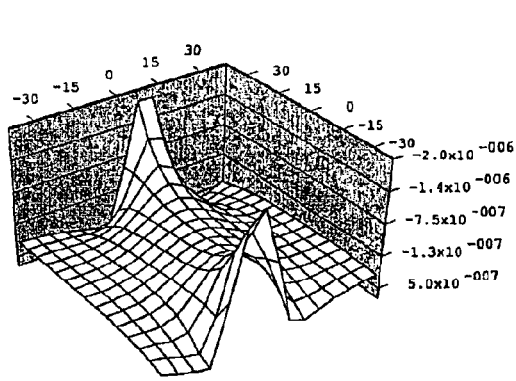
FIG. 10 is the sensitivity distribution from the voltage measurement opposite to the current excitation using the adjacent sensing strategy.
Figure 11:
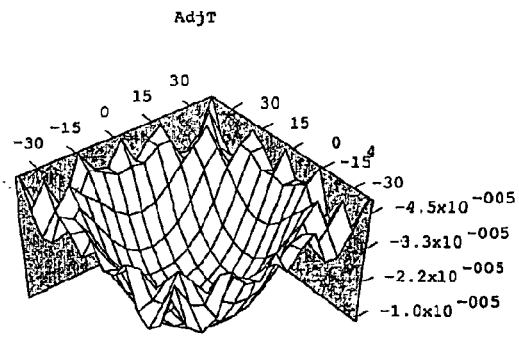
FIG. 11 is the overall sensitivity map using adjacent sensing strategy.

FIG. 8 shows one of the sensitivity maps relating to the measurement position opposite to the current injection. Summing the coefficients from the seventy-two normalised sensitivity maps at each pixel, it gives an overall sensitivity distribution as FIG. 9. To compare the sensitivity homogeneity, two related sensitivity maps obtained from adjacent sensing strategy are given in FIG. 9 and FIG. 10. It can be seen that FIG. 8 gives a more homogenous sensitivity band across the central area, compared to FIG. 10. The overall sensitivity distribution in FIG. 9 is more homogenous as well, compared to that given in FIG. 11, which demonstrates that a much improved total-sensitivity distribution over the sensing area has been produced. The results of the alternative sensing strategy imply that the imaging sensitivity can be relatively intensified or attenuated at a particulate interested area in the whole imaging domain. The sensitivity matrix for such specific distribution can be derived from either the alternative sensing strategy or the particulate combination of the sensitivity matrix derived from a known basic set of independent measurements (e.g. adjacent electrode pair sensing strategy).

The sensor geometry and its conductivity value can be further optimised.

It is found that the ill conditioning of the sensitivity matrix (essentially Jacobean matrix) is related to the non-homogeneity of the sensitivity field. The bigger the condition number of the sensitivity matrix is, the more non-homogeneous the sensitivity field is. The smallest sensitivity is related to the central elements with largest related to periphery elements [Yorkey, et al, IEEE Trans. Biomed. Eng., BME 34(11), 1987]. Take the condition number as the optimum objective, we can optimize the conductive ring sensor against different thickness and conductivity of the conductive ring sensor.

Figure 12:
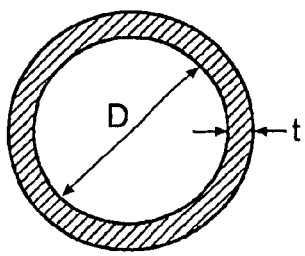
FIG. 12 is the definition of the sensor geometry.

FIG. 12 shows the sensor geometry used during the optimum design. Here, sixteen electrical contacts are distributed around the conductive ring, possessing half of the circumference of the external side of the ring. The ring itself has an internal diameter of 5 cm. The conductive ring thickness, t, was varied during the simulations. The value of t was assumed to be 0.2 cm, 0.6 cm, 0.8 cm, and 1.0 cm. The conductivity of the ring is also a variable ranging from 0.11 ms/cm to 0.66 ms/cm. The sensor was assumed filled with water with a conductivity of 0.11 ms/cm.

Figure 13:
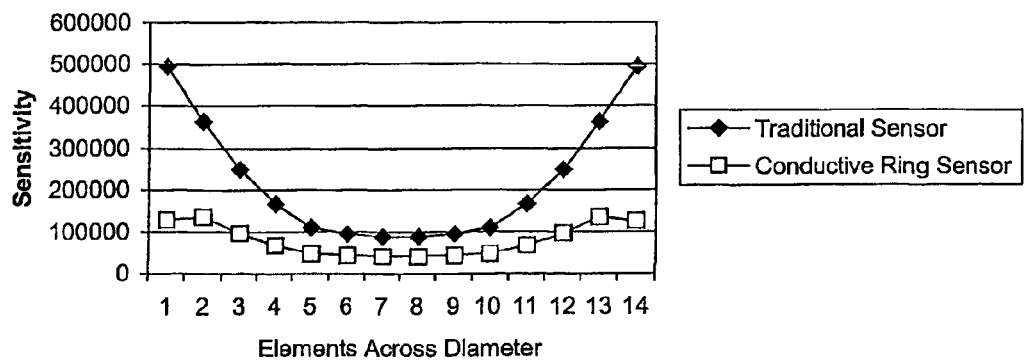
FIG. 13 shows a comparison of sensitivity of two sensors at the elements across the FIG. 14 demonstrates the distribution of the illness measure (condition number)

A comparison of sensitivity distribution across the diameter is shown in FIG. 13, where the current is injected from electrode 1 and 2 with measurements taken from electrodes 9 and 10. The distribution in the conductive ring sensor shows more homogenous than that in traditional sensors.

It is worth to mention that the important parameters are the ratio of the conductivity and thickness of the ring to those of the material filling the sensor, rather than their absolute values. For example, the numerical results for one case could be obtained from another case by appropriate scaling if the same conductivity and thickness ratio were used in simulations.

Figure 14:
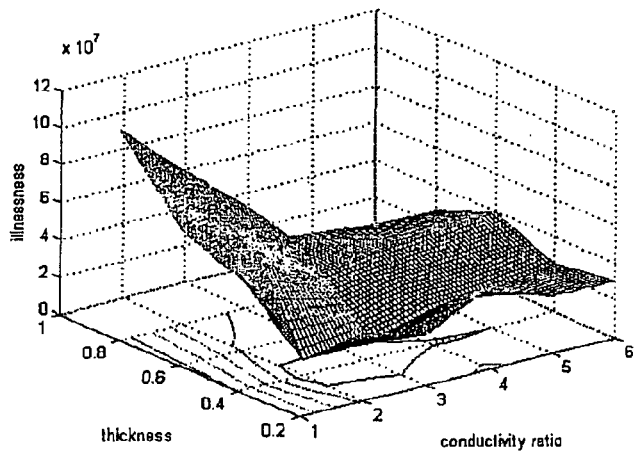

A sensitivity matrix for a commonly used adjacent sensing protocol [Brown et al, Proc. IEE Int. Conf. on Electric and Magnetic field in Med. and Bio, 1985] is computed and condition number calculated for each conductivity and thickness value. FIG. 14 shows the distribution of the condition number of the sensitivity matrix when the thickness and conductivity of the conductive ring sensor varies.

From FIG. 14, we could find that within a modest range of conductivity, the illness measure (the condition number) decreases with the increase of the conductivity and the thickness of the conductive ring sensor, as was confirmed by visualisation with Maxwell 2D simulations.

Figure 15:
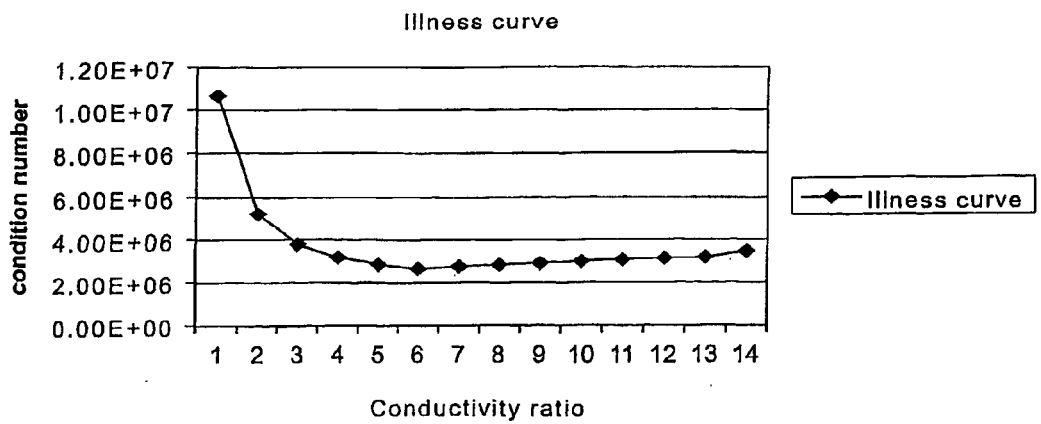
FIG. 15 gives the illness curve (a conductivity ratio of 1 stands for conventional sensor)

It is important to note that the illness measure is not a monotonously decreasing function of the thickness and conductivity of the conductive ring sensor. As an example, when the thickness of the conductive ring sensor is fixed at 1, and the conductivity of the conductive ring sensor is a variable, the condition number curve is shown in FIG. 15. It is found that the illness measure reaches its minimum at the conductivity of 0.66 ms/cm. In FIG. 14, apparently, the optimal parameters of the conductive ring should be 0.55 ms/cm and 4 mm for the conductivity and the thickness respectively.

Figures 16A, 16B:
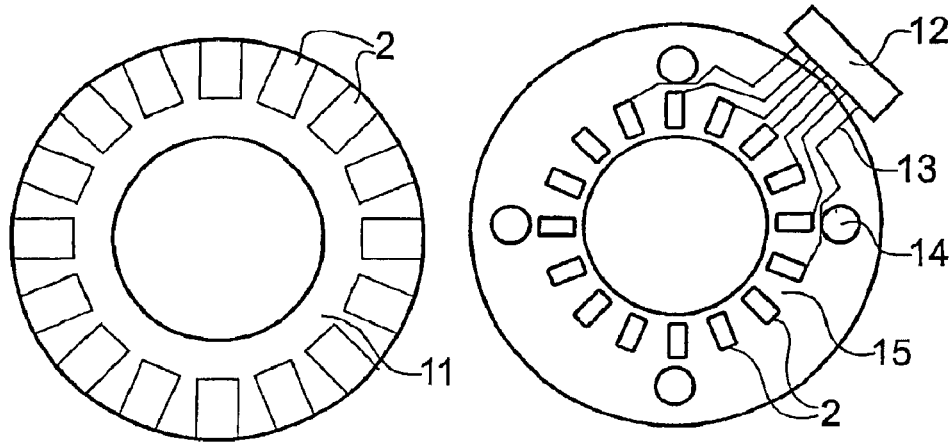
FIG. 16 shows alternative constructions of the conductive sensor.

In addition to the traditional "tube" shape sensor configuration, the sensor can also be constructed from a conductive disk 11. A hole is drilled in the center of the disk and a layer of metallic coating serving as electrode contacts 2 is made around the ring. [FIG. 16a].

Figure 16C:
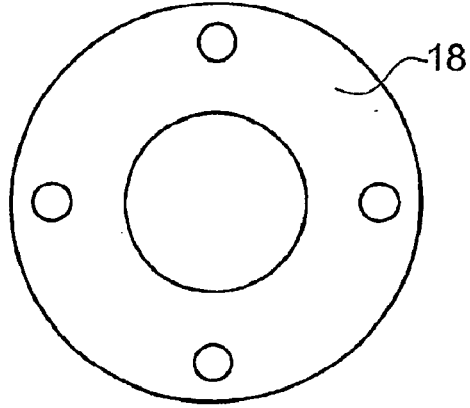

The disk shape sensor can also be configured into a flange or a washer from 18 [FIG. 16c]. In order to facilitate the wiring, PCB 15 can be made to integrate the electrical contacts 2, wiring 13 and connector 12 [FIG. 16b]. Another advantage of this configuration is its flexibility for replacing the conducive ring once it is contaminated such as in food or pharmaceutical applications.

Following the idea above, the conductive sensor can be made in a micro- or nano-scale using micro-machine technology or integrated circuit fabrication technologies.

The sensor can also be fabricated integrated with its processing circuits on a single silicon chip.

The sensitivity theorem deduced by Geselowitz [IEEE Trans. BME-18, 1971] and later refined by Lehr [IEEE Trans. BME-19, 1972] for a two ports system can be expressed in discrete domain as Equation 3 [Murai, et al, IEEE Trans. BME-32, 1985] and Equation 4 [Wang, et al, Chem. Eng. Comm. V175, 1999], assuming the conductivity change is much smaller than the original value ($\Delta\sigma_k<<\sigma_k$) and neglecting the high order terms and supposing that the conductivity distribution is composed from w small uniform 'patches' or pixels. In this case, the sensitivity coefficient, s, for each discrete pixel is given by Equation 5 [Murai, et al, IEEE Trans. BME-32, 1985], where $\eta_k$ is a discrete area at k.

$$\Delta Z = \sum_{k=1}^{w} \Delta\sigma_k s_{\phi,\psi,k} \quad \text{(Equation 3)}$$

$$Z = -\sum_{k=1}^{w} \sigma_k s_{\phi,\psi,k} \quad \text{(Equation 4)}$$

$$s_{\phi,\psi,k} = -\int_{\eta_k} \frac{\nabla\phi}{I_\phi} \cdot \frac{\nabla\psi}{I_\psi} \cdot d\eta_k \quad \text{(Equation 5)}$$

where $\psi_{AB}$, $\phi_{CD}$ are potentials measured from ports A-B and C-D in response to the present of currents $I_\psi$ and $I_\phi$, respectively.

In practical applications of electrical impedance tomography, image reconstruction was highly affected by the electrode modelling error and the measurement noise. In practice, it was hard to make the electrode system oily consistent (e.g. geometry, electrode-electrolyte interface, installation environment, etc.). Quality of data acquired under industrial environment was also decayed by industrial and instrumental noises.

Normalisation procedure has been employed in almost all back-projection algorithms. The normalisation procedure, as given in Equation 6, can be derived from dividing Equation 3 by Equation 4, $$\frac{\Delta V_j}{V_j} = -\frac{\sum_{k=1}^{w} \Delta \sigma_k s_{j,k}(\sigma_k)}{\sum_{k=1}^{w} \sigma_k s_{j,k}(\sigma_k)} \quad ((\Delta\sigma_k \ll \sigma_k, j=1,2,\ldots,P)) \quad (6)$$

Where j is the measurement-projection location and k is the pixel number, $s_{jk}$ denotes the sensitivity coefficient at pixel k under the measurement-projection j, P denotes the maximum number of measurements, w denotes the maximum number of pixels, $\sigma_k$ and $\Delta\sigma_k$ are the conductivity and conductivity change at pixel k, respectively, and $V_j$ and $\Delta V_j$ are in respect to the reference voltage and the voltage change at measurement-projection j.

The problem of conductivity distribution is of a nonlinear type. As the sensitivity theorem is based on a linear approximation with a condition $\Delta\sigma_k \ll \sigma_k$, therefore, an iterative approach was employed in many cases to approach the true value. Both forward and inverse solution procedures have to be employed in the multi-step solution, which are used for error estimation and updating, and resulting a step solution respectively. Conjugate gradients (CG) method is utilised to solution the linear equations in both forward and inverse problems. In this patent this method is named as sensitivity theorem based inverse solution using conjugate gradient methods (SCG).

Forward solution in the multi-step inverse solution is used for producing an error vector for each step inversion. It also up-dates the sensitivity matrix for next step inverse solution. Sensitivity matrix can be derived directly from the nodal voltages obtained from the forward solution [Yorkey, et al, IEEE Trans. BME-34, 1987, Murai, et al, IEEE Trans. BME-32, 1985]. The actual current value used in the solution is not significant as long as the value doesn't vary in whole process since only relative changes of the boundary voltage measurements are employed in following inverse solution.

The solution of a FEM model presenting a 2D cross-section of a process vessel with Neumann boundary conditions in addition to a single Dirichlet condition to avoid singularity can be solved by Equation 7 utilising a linear approximation given by Yorkey et al and Murai et al. [Yorkey, et al, IEEE Trans. BME-34, 1987, Murai, et al, IEEE Trans. BME-32, 1985].

$$Yv = c \quad (7)$$

where Y, v, c denotes the global conductance matrix, the nodal voltage vector, and the nodal current vector respectively.

Based on the expression given by Eq.6 and the assumption of a homogenous conductivity distribution, $\sigma_o$, at the time of taking reference V, the inverse solution in the multi-step approach is given by Eq.8 in the form of matrix notation, $$\gamma = -\bar{s}^{-1} \cdot e \quad (8)$$

where the elements of the normalised sensitivity matrix $\bar{s}^{-1}$ at the iteration n, the vector of conductivity relative change $\gamma$ at pixel k, and the vector of boundary relative change e at projection j are denoted as Eq.9, Eq.10 and Eq.11, respectively. The conductivity is updated by Eq.12.

$$\bar{s}_{j,k}^{(n)} = \frac{s_{j,k}(\hat{\sigma}_k^{(n)})}{\sum_{k=1}^{w} s_{j,k}(\hat{\sigma}_k^{(0)})} \quad (9)$$

$$\gamma_k^{(n+1)} = \frac{\Delta\hat{\sigma}_k^{(n+1)}}{\hat{\sigma}_k^{(0)}} \quad (10)$$

$$e_j^{(n)} = \frac{\Delta V}{V} = \frac{V_j'(\sigma') - V_j(\sigma)}{V_j(\sigma)} \quad (11)$$

$$\hat{\sigma}_k^{(n+1)} = \hat{\sigma}_k^{(n)}(1 + \gamma_k^{(n+1)}) \quad (12)$$

where $\sigma$ and $\sigma'$ are actual conductivity distribution at the moment of acquiring the reference voltage V and measurement V'. $\hat{\sigma}_k^{(o)}$ and $\hat{\sigma}_k^{(n)}$ are estimated conductivity values for simulating $\sigma$ and $\sigma'$.

Since conductivity is inversely related to voltage, the conductivity updating also can be based on an approximation of the inverse relation (Eq.13 based on $1+x \approx 1/(1-x)$ at $x<1$), which can improve the convergence speed for both positive and negative changes in conductivity.

$$\hat{\sigma}_k^{(n+1)} \approx \frac{\hat{\sigma}_k^{(n)}}{1 - \gamma_k^{(n+1)}} \quad (13)$$

Noting the validating condition $\Delta\sigma \ll \sigma$, the $s_{j,k}(\hat{\sigma}_k^{(o)})$ in response to $u_j(\hat{\sigma}_k^{(o)})$ as well as the regularisation procedure in the linear approximation Eq.6, Eq.11 thus decomposes to $$e_j^{(n)} = \frac{V_j'(\sigma')}{V_j(\sigma)} - \frac{u_j'(\hat{\sigma}_k^{(n)})}{u_j(\hat{\sigma}_k^{(0)})} \quad (14)$$

where the $u_j(\hat{\sigma}_k^{(o)})$ and $u'_j(\hat{\sigma}_k^{(n)})$ are the estimated reference voltage and updated measurement voltage in respect to the conductivity distribution $\hat{\sigma}_k^{(o)}$ and $\hat{\sigma}_k^{(n)}$. After a number of steps of updating the conductivity distribution and the sensitivity matrix, the decomposed boundary relative change or error vector in Eq.14 will be minimised. It is thought the non-linear inverse solution has been reached when the norm of the error vector is sufficiently small.

The procedure of multi-step iteration is performed as follows.

(1) Pre-compute the assumed boundary voltage vector and the sensitivity matrix, $$u(\sigma^{(o)}), s(\sigma^{(o)})$$

(2) Measure the boundary voltage profiles and produce the relative change vector, $$\eta_j = \frac{V_j'(\sigma')}{V_j(\sigma)}$$

$$(j=1,2,\ldots,P)$$

(3) Pre-set the iteration control factors for the minimum convergence error, $\epsilon_S$, the maximum number of inverse steps, $\delta_S$, and the maximum number of iterations, $\delta_C$, for the GCG.

(4) Initiate the first estimations for the error function vector and the conductivity vector, $$e^{(1)} = [\bar{e}_1^{(1)}, \ldots, \bar{e}_P^{(1)}]^T, \quad \bar{e}_j^{(1)} = \eta_j - \sum_{j=1}^{P} \eta_j / P$$

$$\hat{\sigma}^{(1)} = [\hat{\sigma}_1^{(1)}, \ldots, \hat{\sigma}_w^{(1)}]^T, \quad \hat{\sigma}_k^{(1)} = \sigma_0 \bigg/ \left(\sum_{j=1}^{P} \eta_j / P\right)$$

(5) Normalise the sensitivity matrix (the iteration steps n is from 1 to $\delta_S$)

$$\bar{s}_{j,k}^{(n)} = \frac{s_{j,k}(\hat{\sigma}_k^{(n)})}{\sum_{k=1}^{w} s_{j,k}(\hat{\sigma}_k^{(0)})}$$

(6) Solve the inverse problem using the GCG method and then update the relative change in the conductivity vector (Maximum Iteration=$\delta_C$), $$\gamma = -\bar{s}^{-1} \cdot e$$

(7) Update the conductivity vector, $$\sigma^{(n+1)} = \sigma^{(n)} \cdot (1 + \gamma^{(n+1)})$$

(8) Solve the forward problem using the ordinary CG method to update the boundary voltage vector and sensitivity matrix, $$u(\sigma^{(n+1)}); s(\sigma^{(n+1)})$$

(9) Update the error vector, $$e_j^{(n+1)} = \eta_j - \frac{u_j'(\hat{\sigma}_k^{(n+1)})}{u_j(\hat{\sigma}_k^{(0)})}$$

(10) Check the control factors to determine whether one of them has been reached, $$\|\bar{e}\| \leq \epsilon_s \text{ or Steps} \geq \delta_s?$$

Figure 17:
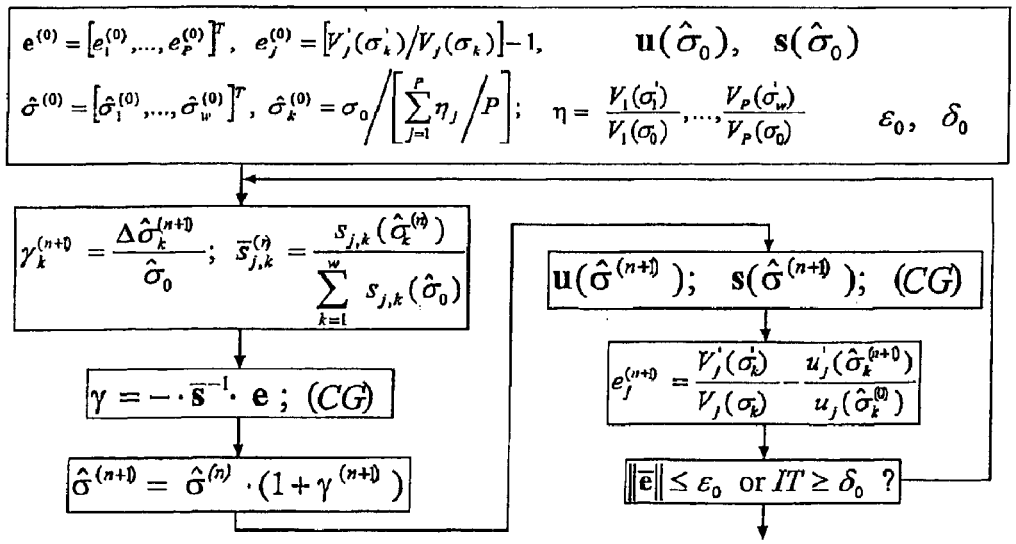
FIG. 17 is a flow chart of SCG reconstruction procedure.

(11) If the convergence or the number of maximum iterations is not reached, the. process jumps to step (5) until one of these conditions is reached. To summarise the procedure, its flowchart is given as FIG. 17.

The sensitivity coefficient back-projection approximation method (SBP), utilising a normalised transpose matrix of the sensitivity matrix obtained from Eq.5 as a weighting matrix, was first refined for ERT by Kotre [Kotre, Physiology Measurements, 15, Suppl. 2A 1992]. The approximation has been successfully applied to many industrial applications [Williams et al, Process tomography—principles, techniques and applications, Butterworth-Heinemann Ltd., 1995] due to its good anti-noise capability and fast solution speed. The physical definition may follow the basic principle of linear back projection: the relative change of the boundary voltage measurements is linearly back-projected to each pixel between two equipotential lines in the case of the equipotential back projection [Baber et al, Applied potential tomography', J. Phys. E: Sci. Instrum., 17,1984], or over whole domain in the case of the SBP [Kotre, Physiology Measurements, 15, Suppl. 2A 1992]. The sum of the products of the relative change and the weight factor/sensitivity coefficient at each pixel, normalised by the sum of their weight factors/sensitivity coefficients that are derived from all possible boundary measurements, approximately presents the relative change of the conductivity at this pixel.

To investigate the accuracy and the limitation of the multi-step solution, a sequence of images were reconstructed from simulated data. A part of these results are presented in this patent. Only the adjacent sensing strategy [Brown et al, Proc. IEE Int. Conf. on Electric and Magnetic field in Med. And Bio., 1985] was employed in these simulations. All references were taken from a homogeneous set-up with a conductivity of 0.11 mS/cm. Meshes with 104 and 224 triangle pixels were used for simulating boundary voltages from these conductivity set-ups. To investigate the discretization error and mesh adaptability of the algorithm, some images were reconstructed using the mesh with 224 elements for data simulated using the mesh with 104 element. Electrode positions at the 224 element mesh also has an 11.25°, anticlockwise rotation compared to those in the simulated set-ups with 104 element mesh.

Considering the importance of the SBP in current applications, these simulated data were also reconstructed using the SBP. A mesh with 316 square pixels was employed for the SBP algorithm. The electrode position at the square mesh has an 11.25° anticlockwise rotation compared to those in the simulated set-ups with the 104 element mesh.

To assess the imaging capability of the SCG algorithm, a Newton-Raphson method based algorithm with Tikhonov regularisation [Vaukonen, Scientific Abstracts of 2nd EPSRC Engineering Network Meeting, UCL, London, 2000], named as EIDORS (EIT and Diffuse Optical Tomography Reconstruction Software, UMIST 2000), is introduced to reconstruct a part of these data. These images are reconstructed using a mesh with 492 elements and parameters of the simulated contact impedance=0.005 Ω/cm, Tikhonov regularization parameter=0.001 and the iteration number=6. The electrode position also has a clockwise rotation compared to the simulation set-up. The original simulated data are directly used for reconstructing images with the EIDORS. However, the data obtained from real measurements have to be regularised by applying the products of relative changes and the standard boundary voltages from a homogeneous set-up in the EIDORS.

Figure 18A:
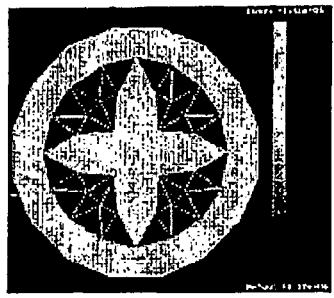
FIG. 18 is reconstructed images from simulated data with large conductivity distribution difference. (a) conductivity set-up with two conductivity values, 0.11 and 0.14 mS/cm, (b) image obtained from the MSBP, (c) image obtained from the EIDORS with 6 steps of solution (Tikhonov regularisation parameter $1\times10^{-3}$), (d, f) images obtained from the SCG with 5 steps of solution and 20 iterations taken in the GCG for solving each inverse function, (e) reconstruction convergence from (d).
Figure 18B:
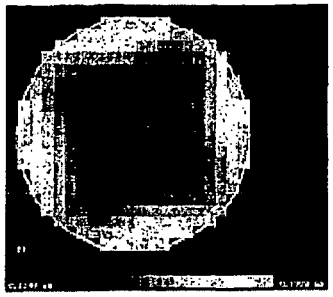
Figure 18C:
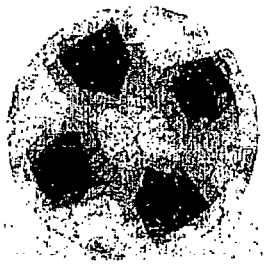
Figure 18D:
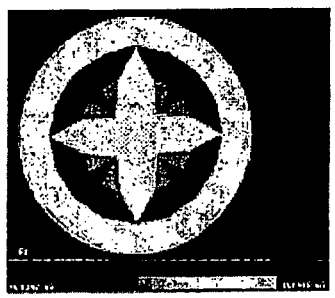
Figure 18E:
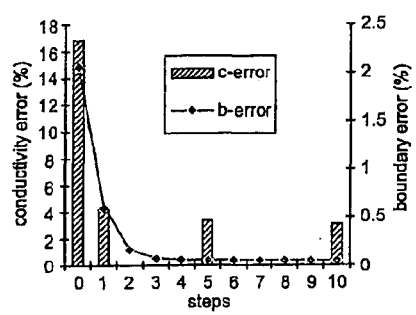
Figure 18F:
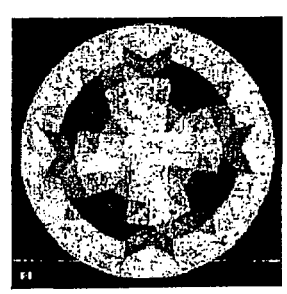
Figure 19A:
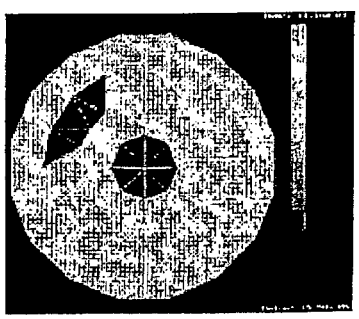
FIG. 19 is reconstructed images for investigating imaging distiguishability. (a) conductivity set-up with two conductivity values, 0.055 and 0.11 mS/cm, (b) image obtained from the MSBP, (c) image obtained from the EIDORS with 6-steps of solution (Tikhonov regularisation parameter $1\times10^{-6}$), (d, f) image obtained from the SCG with 20 steps of solution and 20 iterations taken in the GCG for solving each inverse solution, (e) reconstruction convergence from (d)
Figure 19B:
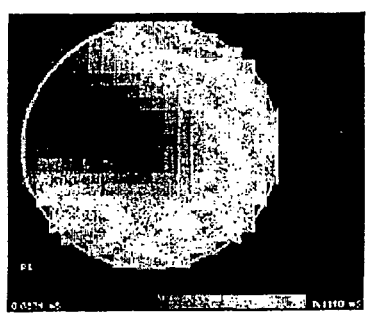
Figure 19C:
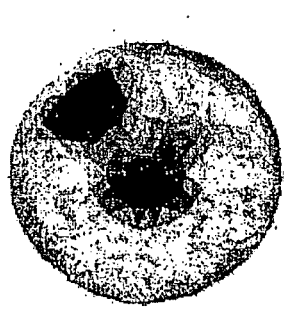
Figure 19D:
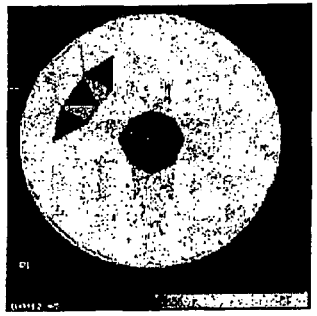
Figure 19E:
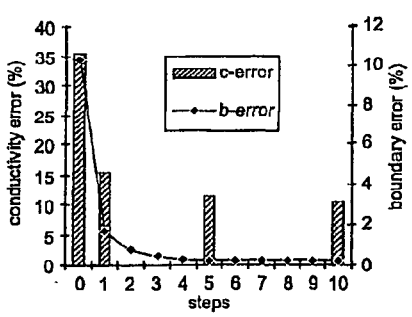
Figure 19F:
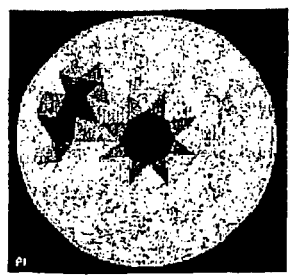

A set-up with a complex conductivity distribution, as shown in FIG. 18a, is reconstructed as FIGS. 18b and 18c from the SBP and EIDORS algorithms respectively. It is obvious that the SBP algorithm could not deliver an accurate image for this set-up (FIG. 18b). Both the EIDORS (FIG. 18c) and SCG (FIG. 18d & f) can reconstruct the complexity of the set-up. The image obtained from five steps of the SCG solution (FIG. 18c) provides a conductivity error of 3.32% and a boundary voltage error of 0.055%. The discretisation error caused by applying different mesh is reflected in FIG. 3f.

Imaging distinguishability of these algorithms was investigated and the results are given in FIG. 19. Two 'objects' were located along a radius of a mesh (FIG. 19a). For the set-up, SBP can image the presence of the two objects but could not distinguish them (FIG. 19b). The edge of the objects' image is also merged with the boundary. The image obtained from EIDORS (FIG. 19c) gives a better presentation about the object location with a clear separation from the boundary but is incapable of distinguishing between the two objects. SCG can clearly distinguish between the two objects although a certain artificial background noise presents (FIG. 19d & f).

Increasing the number of steps to solve the non-linear problem may improve the imaging accuracy. However, the most significant contribution is from the first step, which has already been shown in previous convergence graphs. Therefore, in practice, a single step solution would be widely acceptable for the balance of the imaging accuracy and speed.

The single step method solution is be further simplified by obtaining an approximation of the inverse of $\bar{s}$ ($\bar{s}$ is the normalised sensitivity matrix) and therefore the whole computation for reconstructing a single image only involves a multiplication of a matrix and a vector. The detailed information is provided as following.

The inverse solution can be denoted by equation (15) in a matrix form $$e = -\bar{s} \cdot \gamma \quad \text{(Equation 15)}$$

Where $\bar{s}$ is the normalized sensitivity matrix, $\gamma$ the conductivity relative change vector, and e the boundary relative change vector.

Since $\bar{s}$ is neither square nor positively definite, direct solution to equation (15) using CG method would not exist. In order to be solved, equation (15) has to be transformed to equation (16) by applying minimization to equation (15).

$$\bar{s}^T e = -\bar{s}^T \bar{s} \gamma \quad \text{(Equation 16)}$$

With $\bar{s}^T \bar{s}$ presenting a very large condition number, equation (16) cannot be solved using direct inverse method aiming to an accurate solution. An iterative method with finite steps gives equation (16) an approximation solution, which serves as a kind of regularization. Although being able to provide a sensible solution to equation (16), iterative methods involves much larger computation load than direct inverse methods by which an inverse matrix for $\bar{s}^T \bar{s}$ can be obtained, and the solution to equation (16) only involves a multiplication of a matrix $(\bar{s}^T \bar{s})^{-1} \cdot \bar{s}^T$ with an vector e.

A method of obtaining $(\bar{s}^T \bar{s})^{-1}$ using CG method and therefore providing a one-step solution to equation (16) is presented, having the advantages of both lower computation load and a sensible solution.

To simplify notations, let $A = (\bar{s}^T \bar{s})^{-1}$, and form n equations in (17).

$$A^* x1 = \begin{bmatrix} 1 \\ 0 \\ \cdot \\ \cdot \\ \cdot \\ 0 \end{bmatrix}, A^* x2 = \begin{bmatrix} 0 \\ 1 \\ \cdot \\ \cdot \\ \cdot \\ 0 \end{bmatrix}, A^* x3 = \begin{bmatrix} 0 \\ 0 \\ 1 \\ \cdot \\ \cdot \\ 0 \end{bmatrix}, \ldots A^* xn = \begin{bmatrix} 0 \\ 0 \\ \cdot \\ \cdot \\ \cdot \\ 1 \end{bmatrix}. \quad \text{(Equation 17)}$$

Solving equations (17) using CG method with finite steps (typically 20), we can get vectors, x1, x2, x3 . . . . xn, which can be assembled into [x1, x2, . . . xn], an approximation of $(\bar{s}^T \bar{s})^{-1}$.

Knowing $\bar{s}$, $(\bar{s}^T \bar{s})^{-1} \cdot \bar{s}^T$ can be pre-calculated and therefore equation (16) can be solved in one step. Let $\Gamma^* = (\bar{s}^T \bar{s})^{-1} \cdot \bar{s}^T$, then the reconstruction process can be denoted as:

$$\sigma = \sigma_o^*(1+\gamma) = \sigma_o^*(1-\Gamma^* e) \quad (18)$$

Application 1

Figure 20:
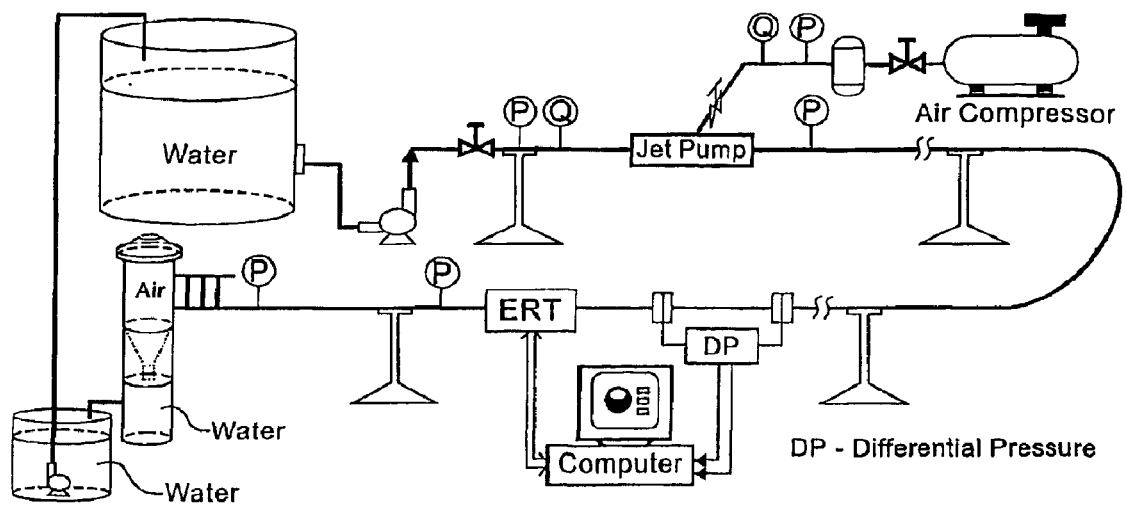
FIG. 20 is a schematic layout of the 20 meters flow loop used for the experiment.

Multiphase flow exists in many industrial processes. The phase distribution and interfaces in a multiphase flow carries significant information about the processes [Chhabra et al, Non-newtonian flow in the process industries— fundamentals and engineering applications, Butterworth-Heinemann, Oxford, 1999]. However its behaviour is extremely complex, which presents a great challenge to the study of the flow mechanisms and the measurement of multiphase flow. Both single modality and multi-modality imaging have been reported [Dyakowski et al, Powder Technol. 104, 1999; Hoyle et al, Proc. 1st World Congress on Industrial Process Tomography, Buxton, UK, 1999] as a means to identity flow regimes in two-phase flow. A direct imaging method for characterising gas-water flow based on a simple 4-electrode technique was proposed [Seleghim et al, Meas. Sci. Technol. 9 1998]. Solid concentration distribution can be imaged using electrical resistance tomography (ERT) and its local velocity profile could be interpreted by applying cross-correlation method for a twin-plane sensing system in a full-filled pipe flow [Lucas et al, Journal of Flow Measurement and Instrumentation, 10, 4,1999]. However, most previous flow applications using conventional electrical resistance tomography were only applied for vertical pipes or horizontal pipes in the absence of large gas bubbles. Signal saturation will occur for a half-filled pipe flow, such as churn flow in a horizontal flow loop, since part of electrodes lose their electrical contacts with the electrically conductive fluid. Imaging methods based on the electrical conductive ring sensing strategy has been used for measuring the two-phase flow with 'electrically continuous' and 'discontinuous' phases. As a preliminary test, several examples of identifying flow regimes using this technique are presented A 20 m flow loop (inner diameter, 50 mm) fitted with ERT sensors was employed for the experiments. A schematic diagram and overview of the flow loop are given in FIG. 20. Mains tap-water (conductivity=0.304 mS/cm) was used as the liquid phase and air, were introduced into the flow loop from a mixing jet-pump. Measurements were performed at ambient temperature. By controlling the air flow-rate at the air inlet of the jet-pump, different flow regimes were generated in the low part of the flow loop.

The experiments were performed under different air flow-rates of 0.5 m³/h, 1.5 m³/h, 2.5 m³/h, 3.5 m³/h and the one less than 0.5 m³/h in regard to the productions of slug flow, slug-churn flow, churn flow and bubbly flow regimes. The water flows were scaled with an accumulating tank during the experiments to get water flow rate and mean velocity. At the mean time, a number of photographs were recorded as visual presentations of these different flow regimes.

Figure 21:
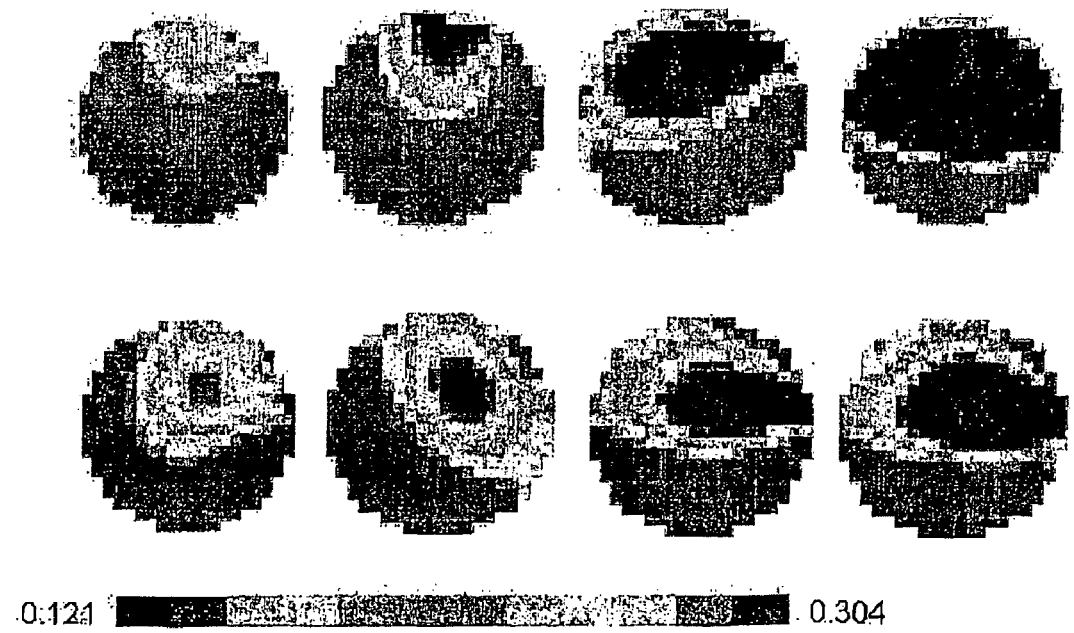
FIG. 21 is reconstructed 2D images in respect to typical air cavity formation in the flow loop.

Two-dimensional (2D) slice images were sequentially reconstructed. Some reconstructed images in respect to typical air cavities in the flow loop are shown in FIG. 21, where the blue areas represent the air cavities or low conductivity regions and the red areas represent the water or high conductivity regions.

Application 2

Figure 22:
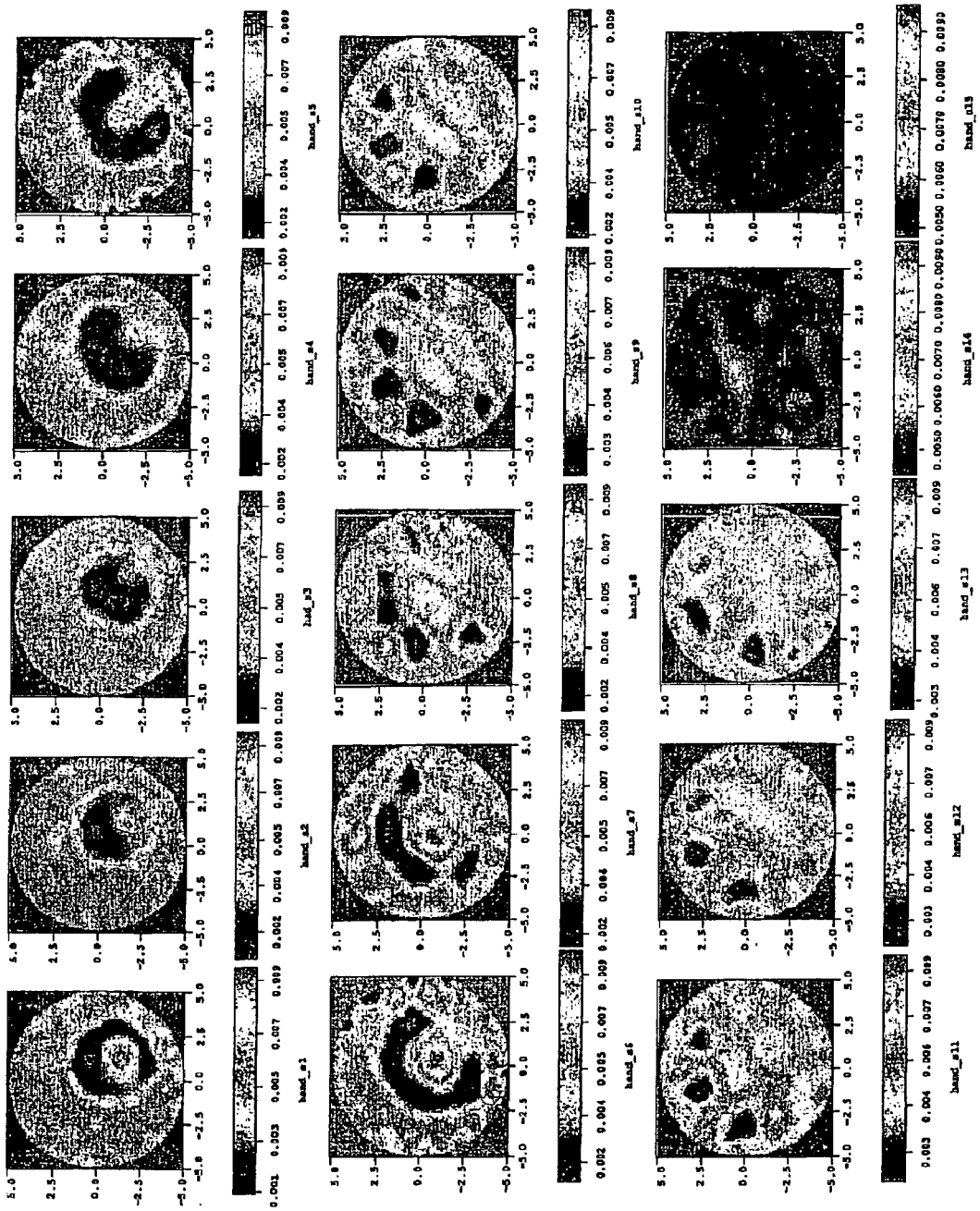
FIG. 22 is a sequence of cross section images of a human hand in 5.16 mS/cm brine, which were reconstructed using STM algorithm with three steps of inversion.
Figure 23:
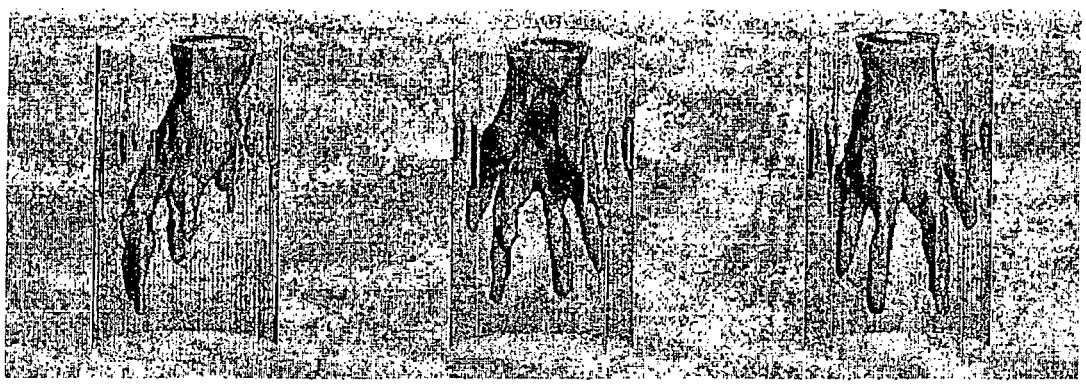
FIG. 23 shows 3-D hand images interpolated from the 2-D EIT images given in FIG. 22 and then iso-surfaced with a cutting value 3.3 mS/cm (Spyglass v1.01).

As an interesting test, a human hand was scanned using an EIT system. A 14.8 cm diameter vessel fitted with one 16-electrode ring sensor and filled with 5.16 mS/cm brine was employed. The adjacent electrode sensing strategy was applied with a pair of 10 mA@9.6 kHz sinusoidal currents for the test. The image data was made up of 15 measurement data sets acquired as the hand moved along the axial direction of the phantom while the water volume was kept the same. The signal-to-noise-ratio (SNR, here is the repeatability of reference voltage) was checked, which was within a maximum error 0.5%. Fifteen 2D images were reconstructed with the SCG [FIG. 22]. These fifteen 2D SCG images were further interpolated to a 3D hand image. A cutting value of 3.3 mS/cm was applied to extract the surface of the hand skin as an iso-surface using Spyglass v1.00. An outline of the human hand has been successfully extracted as shown in FIG. 23. Some distortions can also be found, which may be caused by the electrode noise, the unstable position of the hand during the scanning and the 3-D effect of electrical field.

What is claimed is:

1. A method of measuring the distribution of electrical impedance of a fluid, comprising:

surrounding the fluid with an electrically conductive ring electrode that comprises a plurality of metallic contacts embedded into the conductive ring and spatially distributed around the axis of the ring, in electric contact with an outside wall of the ring;

applying between two contacts, sequentially, an input electrical signal, which while applied to a pair of the contacts, causes respective output signals to be generated between any other pair of contacts;

measuring said output electrical signals between successive pairs of contacts, the contacts of each pair of contacts selected for signal generation and for signal reception, respectively, span an azimuthal angle of about $\pi/2$ with respect to the axis of the conductive ring electrode.

2. A method according to claim 1 wherein the ring electrode has a higher conductivity compared to the principle flow or materials to be measured and it is employed as a ring electrode or part of a sensor body.

3. A method according to claim 2 wherein a relatively homogeneous electric field distribution is produced.

4. A method according to claim 1 wherein the electrically conductive ring comprises at least one of metal, conductive rubber and ceramics.

5. A method according to claim 1 wherein the plurality of metallic contacts penetrate through the outside wall of the ring.

6. A method according to claim 1, wherein a sensitivity distribution of a voltage measurement is intensified at a specific area in the whole of the sensing domain.

7. A method according to claim 1 further comprising deriving an intensified sensitivity matrix from a specific sensing strategy or a combination from a basic sensitivity matrix.

8. A method according to claim 7 wherein the basic sensitivity matrix is derived from equations 1 and 2:

$$Z_{I,J}(I_{M,N}) = \sum_{m=M}^{N-1} \sum_{i=I}^{J-1} Z_{i,i+1}(I_{m,m+1}) \qquad \text{(Equation 1)}$$

$(1 \leq M < N < I < J \leq \text{number of electrode})$ $$s_{I,J,k}(I_{M,N}) = \sum_{m=M}^{N-1} \sum_{i=I}^{J-1} s_{i,i+1,k}(I_{m,m+1}) \qquad \text{(Equation 2)}$$

$(1 \leq M < N < I < J \leq \text{number of electrodes})$.

9. A method according to claim 1 wherein the fluid is selected from a process material, a process fluid and a part of a human body.

10. A method according to claim 1 wherein the fluid has an electrically continuous or discontinuous phase, and wherein the electrically continuous phase is a miscible liquid and the discontinuous phase is in a foam formation or a half filled horizontal oil/water/gas stratified flow.

11. A method according to claim 1 wherein the ring electrode comprises a sensor with discrete electrode structure using an external resistor network connecting all electrodes.

12. A method according to claim 11 wherein a geometry and a conductivity of the conductive ring sensor is optimized using an illness measure of a sensitivity matrix.

13. A method according to claim 11 wherein the sensor comprises a conductive disk, with PCB as its connection.

14. A method according to claim 11 wherein the conductive sensor is made in micro-scale.

15. A method according to claim 14 wherein the micro-scale conductive sensor is made on silicon chips.

16. A method according to claim 15 wherein the micro-scale conductive sensor is integrated with a measurement and processing circuit.

17. A method according to claim 1 further comprising using a multi-step image reconstruction algorithm having an error processing method to reconstruct a conductivity distribution.

18. A method according to claim 17 wherein the following equation is used in the multi-step image reconstruction algorithm:

$$\gamma = -\bar{s}^{-1} \cdot e.$$

19. A method according to claim 18 wherein the error processing method uses the difference between the relative changes of forward solutions and measured results.

20. A method according to claim 19 wherein the following equation is used in the multi-step image reconstruction algorithm:

$$e_j^{(n)} = \frac{V'_j(\sigma')}{V_j(\sigma)} - \frac{u'_j(\hat{\sigma}_k^{(n)})}{u_j(\hat{\sigma}_k^{(0)})}.$$

21. A method according to claim 19 wherein a CG method is used to solve linear equation in implementing both inverse solution and forward solution.

22. A method according to claim 21 wherein the following equation is used in the multi-step image reconstruction algorithm:

$$A^*x1 = \begin{bmatrix} 1 \\ 0 \\ \cdot \\ \cdot \\ \cdot \\ 0 \end{bmatrix}, A^*x2 = \begin{bmatrix} 0 \\ 1 \\ \cdot \\ \cdot \\ \cdot \\ 0 \end{bmatrix}, A^*x3 = \begin{bmatrix} 0 \\ 0 \\ 1 \\ \cdot \\ \cdot \\ 0 \end{bmatrix}, \ldots A^*xn = \begin{bmatrix} 0 \\ 0 \\ \cdot \\ \cdot \\ \cdot \\ 1 \end{bmatrix}.$$

23. A method according to claim 22 wherein the following equation is used in the multi-step image reconstruction algorithm:

$$\sigma = \sigma_0^* (1+\gamma) = \sigma_0^*(1-\Lambda e).$$

24. An apparatus for measuring the distribution of electrical impedance of a fluid comprising:

a cylindrical electrically conductive ring electrode surrounding the fluid, the ring electrode comprising a plurality of metallic contacts embedded into the conductive ring and spatially distributed around the axis of the ring, in electric contact with an outside wall of the ring, the the metallic contacts being responsive to a sequentially applied input electrical signal, which while applied to a pair of the contacts, causes respective output signals to be generated between any other pair of contacts, the contacts of each pair of contacts selected for signal generation and for signal reception, respectively, span an azimuthal angle of about $\sigma/2$ with respect to the axis of the conductive ring electrode.

25. A method of determining an internal structure of a body comprising:

surrounding a body fluid with an electrically conductive ring electrode that comprises a plurality of metallic contacts embedded into the conductive ring and spatially distributed around the axis of the ring, in electric contact with an outside wall of the ring;

applying between two contacts, sequentially, an input electrical signal, which while applied to a pair of the contacts, causes respective output signals to be generated between any other pair of contacts;

measuring said output electrical signals between successive pairs of contacts, the contacts of each pair of contacts selected for signal generation and for signal reception, respectively, span an azimuthal angle of about $\pi/2$ with respect to the axis of the conductive ring electrode.

* * * * *

UNITED STATES PATENT AND TRADEMARK OFFICE
CERTIFICATE OF CORRECTION

PATENT NO. : 6,940,286 B2
DATED : September 6, 2005
INVENTOR(S) : Wang et al.

It is certified that error appears in the above-identified patent and that said Letters Patent is hereby corrected as shown below:

Title page,
Item [57], ABSTRACT,
Line 11, should read -- rent distribution along the ring from other electrical contacts, --.

Column 4,
Line 21, should read -- at the elements across the diameter; --.

Column 16,
Line 66, should read -- respectively, span an azimuthal angle of about π/2 with --.

Signed and Sealed this

Third Day of January, 2006

JON W. DUDAS
*Director of the United States Patent and Trademark Office*